(12) United States Patent
Andersson et al.

(10) Patent No.: US 8,632,843 B2
(45) Date of Patent: Jan. 21, 2014

(54) METHODS AND SYSTEMS OF CONTROLLED COATING OF NANOPARTICLES ONTO MICRO-ROUGH IMPLANT SURFACES AND ASSOCIATED IMPLANTS

(75) Inventors: Martin Andersson, Göteborg (SE); Fredrik Currie, Göteborg (SE); Per Kjellin, Göteborg (SE)

(73) Assignee: Promimic AB, Gothenburg (SE)

( * ) Notice: Subject to any disclaimer, the term of this patent is extended or adjusted under 35 U.S.C. 154(b) by 407 days.

(21) Appl. No.: 12/276,664

(22) Filed: Nov. 24, 2008

(65) Prior Publication Data

US 2010/0131062 A1 May 27, 2010

(51) Int. Cl.
*B05D 1/02* (2006.01)
*B05D 1/40* (2006.01)
*B05D 3/04* (2006.01)
*A61F 2/38* (2006.01)
*A61F 2/32* (2006.01)
*A61F 2/62* (2006.01)

(52) U.S. Cl.
USPC ....... 427/2.24; 427/2.1; 427/2.25; 427/421.1; 427/425; 427/475; 623/20.14; 623/22.11; 623/23.27; 623/39

(58) Field of Classification Search
USPC .......... 427/2.1, 2.24–2.27, 180, 346; 623/11.11, 16.11–23.63
See application file for complete search history.

(56) References Cited

U.S. PATENT DOCUMENTS 5,294,599 A * 3/1994 Shibata et al. ................ 505/440
5,667,385 A * 9/1997 Hansson ..................... 433/201.1
5,762,709 A * 6/1998 Sugimoto et al. ............... 118/52
6,001,426 A * 12/1999 Witherspoon et al. ........ 427/449
6,013,099 A * 1/2000 Dinh et al. .................... 623/1.15
6,013,591 A * 1/2000 Ying et al. ......................... 501/1
6,517,791 B1 * 2/2003 Jaynes .......................... 423/210

(Continued)

FOREIGN PATENT DOCUMENTS

WO   WO 2005123579 A1 * 12/2005

OTHER PUBLICATIONS

Wei Qi Yan et al. Apatite layer coated titanium for use as bone bonding implants. Biomaterials, vol. 18. 1997. pp. 1185-1190.*

(Continued)

*Primary Examiner* — Cachet Sellman
(74) *Attorney, Agent, or Firm* — Myers Bigel Sibley & Sajovec, PA

(57) ABSTRACT

The invention provides methods and systems that control the application of a material onto micro-rough implant surfaces. Thus, the present invention provides method of applying crystalline nanoparticles onto the surface of an implant to produce an implant with a crystalline nanoparticle layer on its surface, the method comprising: providing an implant substrate body; applying crystalline nanoparticles onto the surface of the implant; and rotating the implant, to produce an implant with a crystalline nanoparticle layer on its surface. This method of nanoparticle application is designed to promote the integration of implants, such as dental and orthopedic screws, into living tissue, and offers the ability to control the thickness and uniformity of the nanoparticle layer, in one or several layers, while simultaneously retaining the microroughness of the implant. Further provided are systems for applying crystalline nanoparticles onto the surface of an implant and implants having a crystalline nanoparticle layer on their surfaces.

21 Claims, 10 Drawing Sheets

(56) References Cited

U.S. PATENT DOCUMENTS

| | | | |
|---|---|---|---|
| 7,771,774 B2* | 8/2010 | Berckmans et al. | 427/2.1 |
| 2004/0115239 A1* | 6/2004 | Shastri et al. | 424/423 |
| 2005/0194573 A1* | 9/2005 | Yamashita | 252/500 |
| 2006/0184251 A1* | 8/2006 | Zhang et al. | 623/23.56 |
| 2007/0193509 A1* | 8/2007 | Lawrynowicz et al. | 118/321 |
| 2009/0010990 A1* | 1/2009 | Little et al. | 424/423 |
| 2009/0118829 A1* | 5/2009 | Powell et al. | 623/8 |

OTHER PUBLICATIONS

Ii et al. Hydroxyapatite coating by dipping method and bone bonding strength. Journal of materials Science: Materials in Medicine. vol. 1996.pp. 355-357.*

Lima et al. HVOF Spraying nanostructured hydroxyapatite fir biomedical applications. Materials Science and Engineering A, 396, 1-2, pp. 181-187, 2005.*

Yan et al. "Apatite Layer-Coated Titanium for Use as Bone Bonding Implants" *Biomaterials* 18(17):1185-1190 (1997).

Monmaturapoj, "Nano-size Hydroxyapatite Powders Preparation by Wet-Chemical Precipitation Route" *Journal of Metals, Materials and Minerals* 18(1):15-20 (2008).

J.W. Mullin, "Industrial Techniques and Equipment" *Crystallization*, 4th Ed., pp. 315-319 (2001) Elsevier Ltd. (ISBN 0 7506 4833 3).

Yoruç et al., "Double Step Stirring: A Novel Method for Precipitation of Nano-Sized Hydroxyapatite Powder" *Digest Journal of Nanomaterials and Biostructures* 4(1):73-81 (2009).

* cited by examiner

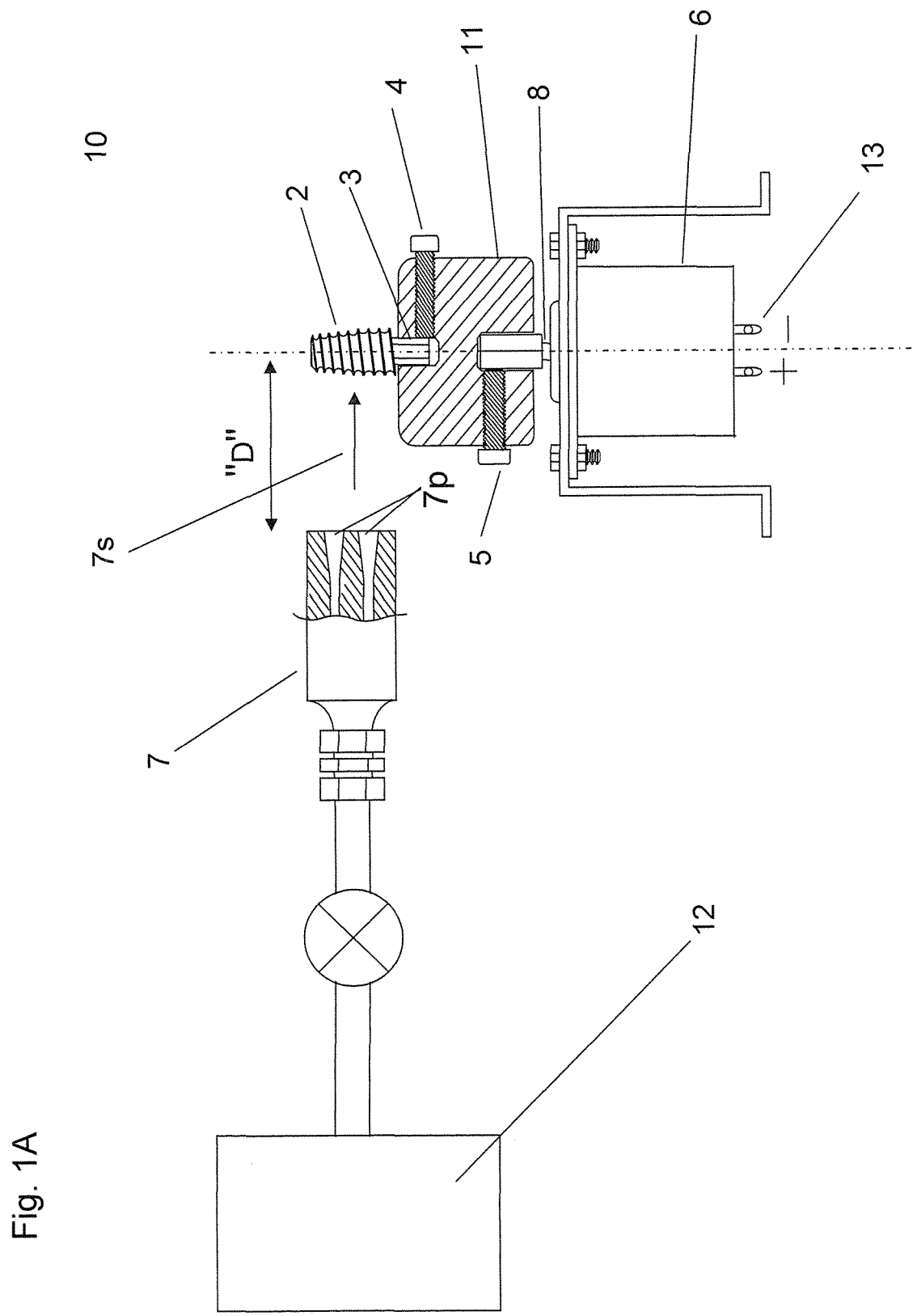

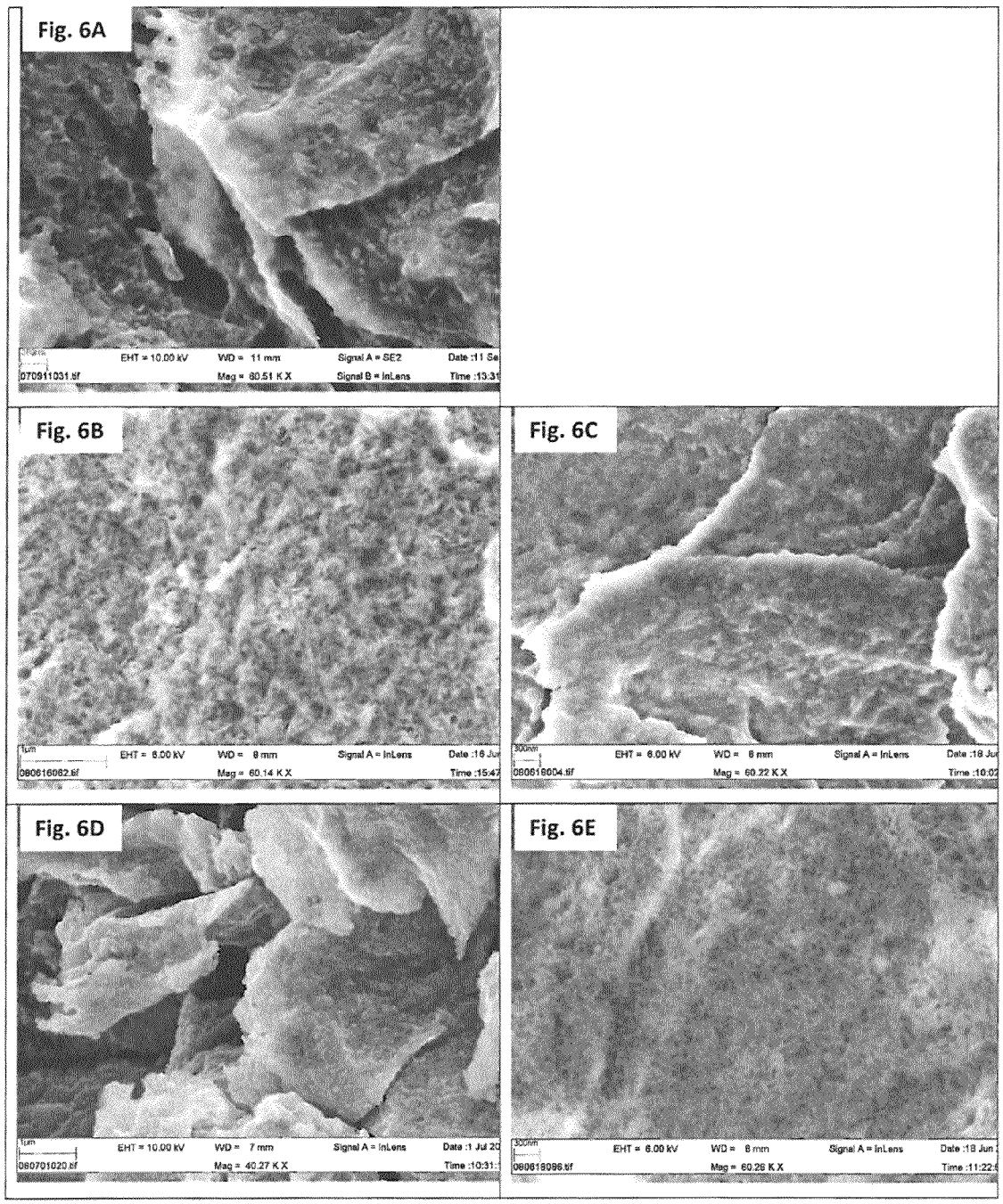

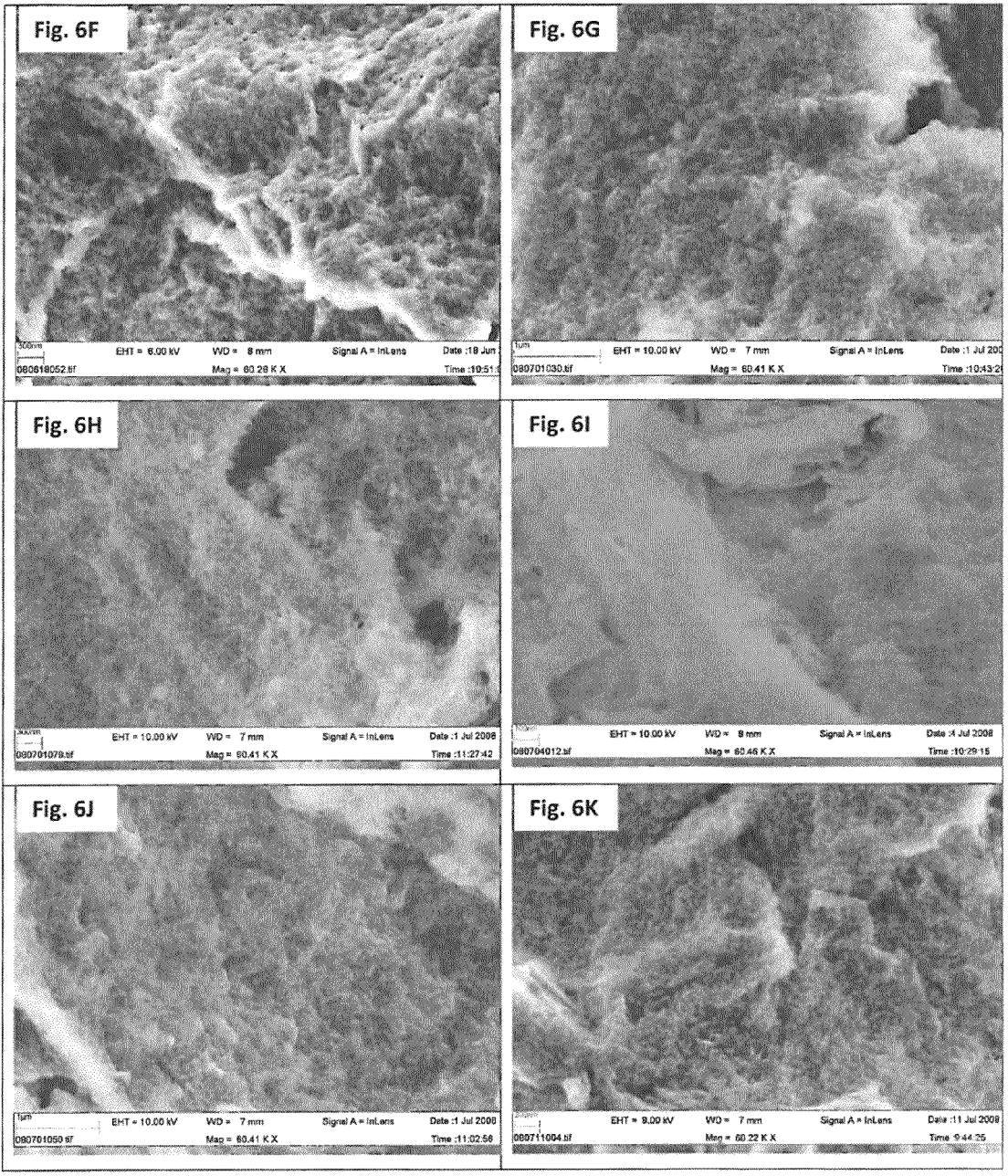

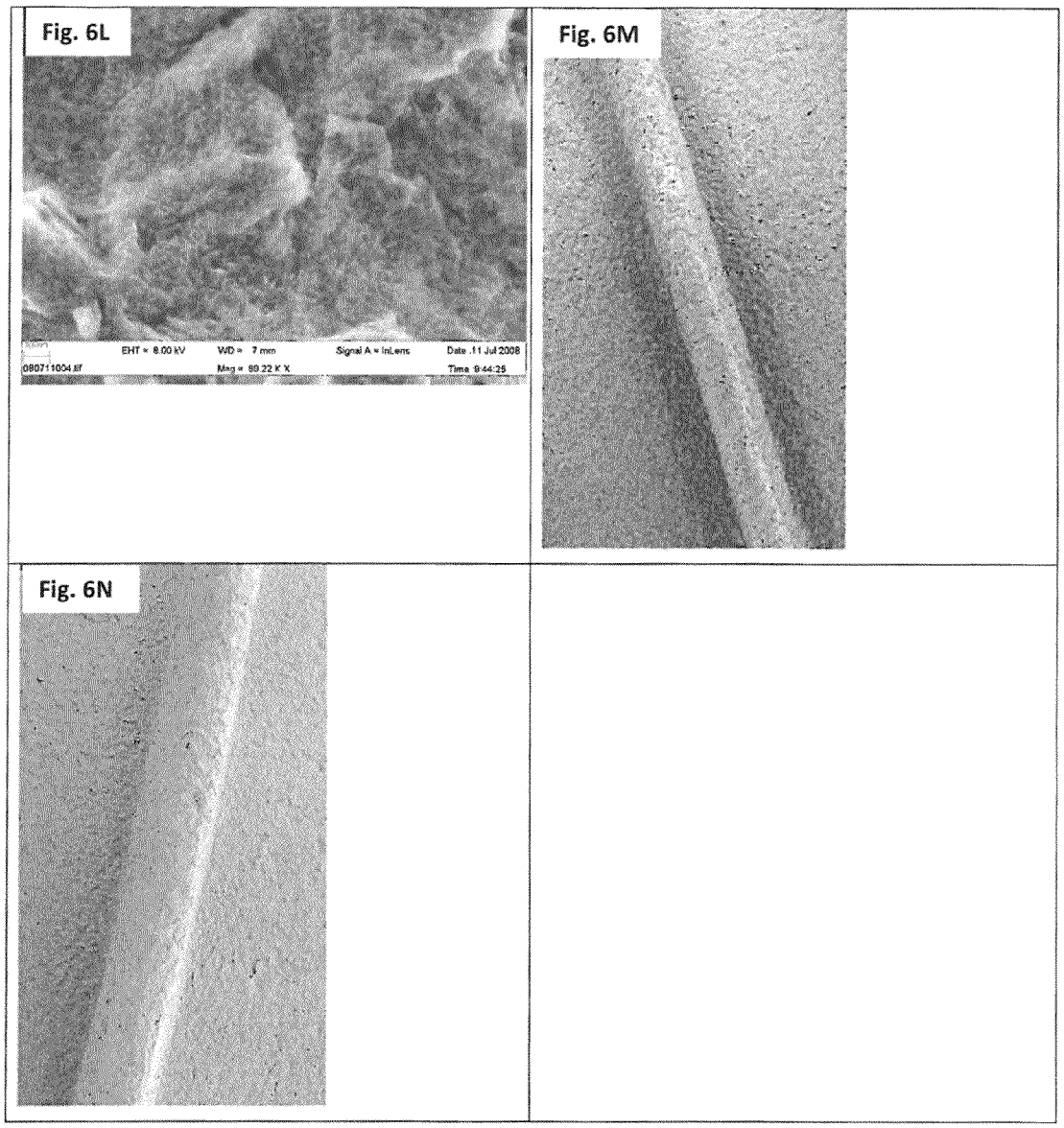

METHODS AND SYSTEMS OF CONTROLLED COATING OF NANOPARTICLES ONTO MICRO-ROUGH IMPLANT SURFACES AND ASSOCIATED IMPLANTS

FIELD OF THE INVENTION

This present disclosure relates to methods and systems that can control the application of a nanosized material onto micro-rough implant surfaces.

BACKGROUND OF THE INVENTION

Implants with the purpose of restoring missing body functions are becoming more common within medicine and health care. Many different types of implants exist and they are produced from a variety of different materials. In the case of osseointegrated implants, which are devices that are surgically implanted and integrated into living bone, the most commonly occurring materials are metals, such as titanium and titanium alloys, and ceramics, such as zirconium oxide. These materials have mechanical properties similar to the replaced bone tissue.

For the implant to function successfully, a good anchoring of the implant is required. This anchoring can be a combination of mechanical attachment and physico-chemical bonding and is dependent on both the micro structure of the implant surface (see, e.g., Wennerberg et al., *J. Biomed. Mater. Res.* 30 (1996) 251-260; U.S. Pat. No. 4,330,891 to Branemark et al.; and U.S. Pat. No. 6,689,170 to Larsson et al.), as well as the surface chemistry (U.S. Pat. No. 5,571,188 to Ellingsen et al.; R. G. T. Geesink, *Clin. Orthop.* 261 (1990) 39-58; Jansen, et al., *Mater. Res.*, 25 (1991) 973-989; Bauer, et al., *J. Bone Joint Surg.*, 73A (1991) 1439-1452; Rashmir-Raven et al. *J. Appl. Biomater.* 6 (1995) 237-242). In order to increase the osseointegration, coatings possessing enhanced osseointegrating properties have been developed. These coatings create an interface between the living tissue and the implant enabling faster and better osseointegration. One common family of coating materials is calcium phosphates and especially the member hydroxyapatite (HA). HA resembles the mineral found in bone and teeth, is chemically stable, and is known to be one of the few materials that are bio-active, meaning it has the property of initiating a physico-chemical bond between the implant material and the surrounding tissue.

Several coating methods exist for deposition of calcium phosphates onto substrates, which includes thermal plasma spray, sputtering, electrochemical deposition and nanoparticle deposition through immersions into particle dispersions. During the thermal plasma spray process, plasma is produced by letting an electric arc pass through a stream of mixed gases. This process results in partial melting of mineral feedstock, which is hurled with a relatively high force at the substrate, for example an implant. This method may, due to the high temperatures involved, affect the crystallinity of the feedstock, creating a mixture of polymorphs as well as amorphous materials. Traditionally, the plasma spray method produces relatively thick coating layers, usually several micrometers, which can create adherence problems between the substrate and the coating, which in turn may lead to poor osseointegration (Cheang, P. and Khor, K. A. *Biomaterials* 1996, 17, 537; Groot et al. *Biomedical. Mater. Res.* 1987, 21, 1375; Story, B. and Burgess, A., S. Calcitek: USA, 1998; and Zyman et al. *Biomaterials* 1993, 14, 225). The thermal plasma spray technique can be used for producing thinner layers, in the order of 100 nanometers (U.S. Pat. No. 5,543,019), but the problems due to the high temperatures still exists.

Sputtering is used to apply sputtered coatings, which are usually non stoichiometric and amorphous, which can cause severe problems with adhesion and a too high coating dissolution rate when implanted. Furthermore, the sputtering method is seldom used due to its low effectiveness and high costs (Massaro et al., *J. Biomedical Materials Research*, 58 (6): 651-657 Dec. 5, 2001). The electrochemical deposition technique is relatively inexpensive, but problems can exist with gas formation during the deposition, resulting in problems with cracking and rupture of the coating. The nanoparticle deposition method uses immersions into particle dispersions. This method results in discrete adsorption of nanoparticles using a one step process in which nanoparticles are deposited on an implant surface where the method requires the surface to be pretreated by roughening at least a portion of the implant surface to produce at least a microscale roughened surface (WO 2008/051555) or as a coating using a two step process involving a pre-treatment of the substrate using silanes (U.S. Patent Appl. No. 2004/0249472). This method demands high quality particle dispersions of well defined nanoparticles, well separated in solutions possessing high wettability of the implant surface.

The nanoparticle deposition methods have been shown to effectively increase the osseointegration, but there are several limitations to these methods, such as the need for the addition of silicon chemicals (aminopropyltriethoxysilane) as well as limitations when controlling the deposition of higher amounts than discrete nanoparticles, as in the case when a layer having a particular thickness is desired. There are several other techniques that are described in the literature, including biomimetic methods where simulated body fluids are utilized to form HA coatings (Wei-Qi Yan et al., *Biomaterials* 1997 (18) 1185-1190), but today it is believed that only the plasma spray and nanoparticle deposition techniques are used commercially. Problems utilizing these above described as well as other techniques not described are plentiful, especially due to that only thick layers can be applied (several µm) leading to problems with adhesion to the substrate and problems with coating objects having complicated shapes. Several of the used or tested techniques also create locally high temperatures, giving amorphous HA instead of the wanted crystalline apatite form. Accordingly, there is a need for new coating methods for the depositions of crystalline nanoparticles, in particular, HA nanoparticles onto surfaces.

Embodiments of the present invention provide methods and systems that can control application of a nanoparticle layer onto micro-rough implant surfaces and associated implants.

SUMMARY OF EMBODIMENTS OF THE INVENTION

Embodiments of the present invention relate to methods and systems that can control the application of a material onto implant surfaces while retaining the underlying microtopography. In addition, disclosed herein are products produced using such methods and systems.

Accordingly, in some embodiments, methods of applying crystalline nanoparticles onto the surface of an implant to produce an implant with a crystalline nanoparticle layer on its surface is provided. The method includes: (a) providing an implant substrate body; (b) applying crystalline nanoparticles onto the surface of the implant; and (c) rotating the implant; to produce an implant with a crystalline nanoparticle layer on its surface. In some embodiments, a gas stream can optionally be directed toward the implant while the implant is rotating The nanoparticle layer on the surface of the implant can enhance the osseointegration of the implant.

In some aspects, the methods include forming a microemulsion containing the nanoparticles by diluting a liquid crystalline phase in which the nanoparticles have been produced. The method can include diluting the liquid crystal containing the nanoparticles, thus forming a water-in-oil microemulsion with a desired concentration of the nanoparticles. Thus, in some embodiments, the applying step can include applying the crystalline nanoparticles when dispersed in a microemulsion.

In some embodiments, the nanoparticles include calcium phosphate nanoparticles. The calcium phosphate nanoparticles can include, but are not limited to, hydroxyapatite nanoparticles. In some embodiments the applying step can be carried out so that the nanoparticles are applied as a thin layer using a liquid deposition technique.

In some embodiments, the method can include rotating or spinning after and/or during the applying of the nanoparticles, thereby controlling the thickness and uniformity of one or more layers of the nanoparticles. In particular embodiments, the implant is rotated after but proximate to the applying step. In some embodiments, a gas stream can be directed toward the implant while the implant is rotating. The methods can control the thickness and uniformity of one or more layers of the nanoparticles. In some embodiments, the methods include controlling the thickness of crystalline nanoparticles and at the same time substantially retaining the microtopography of the implant surface in response to the applying, and rotating steps; and optionally, in response to the directing of the gas step during the rotating step.

In some embodiments, the methods can be used to apply a layer of nanoparticles to the surface of an implant made of metal. The metal can include, but is not limited to, titanium or titanium alloys. In other embodiments, the methods can be used to apply the nanoparticles to a ceramic implant. Ceramic implant material can include, but is not limited to, zirconia.

The methods can be carried out so that the micro roughness of the surface of the implant is substantially retained after the application of the particles.

Furthermore, embodiments of the invention are directed to coating a micro rough implant surface with at least one layer of nanoparticles. In some embodiments, the nanoparticles include a calcium phosphate material, for example hydroxyapatite, which promotes osseointegration. The method can be carried out without pre treating the surface with silanes or roughening the implant surface to produce a microscale surface. In some embodiments, the nanoparticle layer on the surface of the micro rough implant substantially retains the underlying microstructure and promotes the osseointegration of the implant. As discussed above, the thickness of the nanoparticle coating layer can be controlled by spinning or rotating the implant; and optionally, by also directing a gas stream toward the implant during the rotating step. It is noted that with regard to micro rough implant surfaces, the microemulsions of the present invention can penetrate the micro roughened surface, allowing the nanoparticles to reside inside small compartments in the surface of the implant such as nano- or micro sized cracks.

A further embodiment of the present invention provides an implant with a crystalline nanoparticle layer on its surface produced by providing an implant substrate body; applying crystalline nanoparticles onto the surface of the implant; and rotating the implant; to produce an implant with a crystalline nanoparticle layer on its surface. In some embodiments, the method can optionally include directing a gas stream toward the implant while the implant is rotating.

According to other embodiments of the present invention, a titanium implant with a hydroxyapatite nanoparticle layer on its surface is disclosed. The implant is not required to be pretreated prior to applying the crystalline nanoparticles. Yet another aspect of the present invention provides a titanium dental implant comprising a rough titanium surface microtopography with a crystalline hydroxyapatite nanoparticle outer layer, the thickness of the layer being in a range from about 2 nm to about 500 nm. The nanoparticle layer is conformed to the microtopography of the titanium implant surface so that the microtopography can be substantially retained. The nanocrystalline hydroxyapatite nanoparticle layer of the titanium implant is stoichiometric and in a crystalline form.

Other embodiments of the present invention are directed to systems for applying crystalline nanoparticles onto the surface of an implant to produce an implant with at least one crystalline nanoparticle layer on its surface. The systems include: a rotating member; an implant holder attached to the rotating member configured to releasably hold a target implant; and optionally a pressurized gas supply configured to direct a gas stream from the gas supply in a direction that is substantially orthogonal to an implant held by the implant holder.

These and other aspects of the invention are set forth in more detail in the description of embodiments of the invention below.

BRIEF DESCRIPTION OF THE FIGURES

FIG. 1A is a schematic illustration of an exemplary implant spin coater system, according to embodiments of the present invention.

FIG. 6A is a Field Emission Scanning Electron Microscopy (FESEM) image of an unmodified blasted acid-etched titanium implant surface, according to embodiments of the present invention.

FIG. 6B is a FESEM image of a double coated blasted acid-etched titanium implant surface, coated using a rotation speed of 2250 revolutions per minute (rpm), according to embodiments of the present invention.

FIG. 6C is a FESEM image of a double coated blasted acid etched titanium implant surface, coated using a rotation speed of 2250 rpm and a nitrogen flow rate of 40 L/min, according to embodiments of the present invention.

FIG. 6D is a FESEM image of a double coated blasted acid etched titanium implant surface, coated using a rotation speed of 2250 rpm and a nitrogen flow rate of 80 L/min, according to embodiments of the present invention.

FIG. 6E is a FESEM image of a double coated blasted acid etched titanium implant surface, coated using a rotation speed of 3500 rpm, according to embodiments of the present invention.

FIG. 6F is a FESEM image of a double coated blasted acid etched titanium implant surface, coated using a rotation speed of 3500 rpm and a nitrogen flow rate=40 L/min, according to embodiments of the present invention.

FIG. 6G is a FESEM image of a double coated blasted acid etched titanium implant surface, coated using a rotation speed of 3500 rpm and a nitrogen flow rate of 80 L/min, according to embodiments of the present invention.

FIG. 6H is a FESEM image of a double coated blasted acid etched titanium implant surface, coated using a rotation speed of 4700 rpm, according to embodiments of the present invention.

FIG. 6I is a FESEM image of a double coated blasted acid etched titanium implant surface, coated using a rotation speed of 4700 rpm and a nitrogen flow rate of 40 L/min, according to embodiments of the present invention.

FIG. 6J is a FESEM image of a double coated blasted acid etched titanium implant surface, coated using a rotation speed of 4700 rpm and a nitrogen flow rate of 80 L/min, according to embodiments of the present invention.

FIG. 6K is a FESEM image of a single coated blasted acid etched titanium implant surface, coated using a rotation speed of 3500 rpm and a nitrogen flow rate of 40 L/min, according to embodiments of the present invention.

FIG. 6L is a FESEM image of a double coated blasted acid etched titanium implant surface, coated using a rotation speed of 3500 rpm and a nitrogen flow rate of 40 L/min. 50% particle concentration, according to embodiments of the present invention.

FIG. 6M is a FESEM image of a thread of a double coated blasted acid etched titanium implant, coated using a rotation speed of 3500 rpm and no nitrogen flow, according to embodiments of the present invention.

FIG. 6N is a FESEM image of a thread of a double coated blasted acid etched titanium implant, coated using a rotation speed of 3500 rpm and a nitrogen flow rate=40 L/min, according to embodiments of the present invention.

DETAILED DESCRIPTION

Figure 1B:
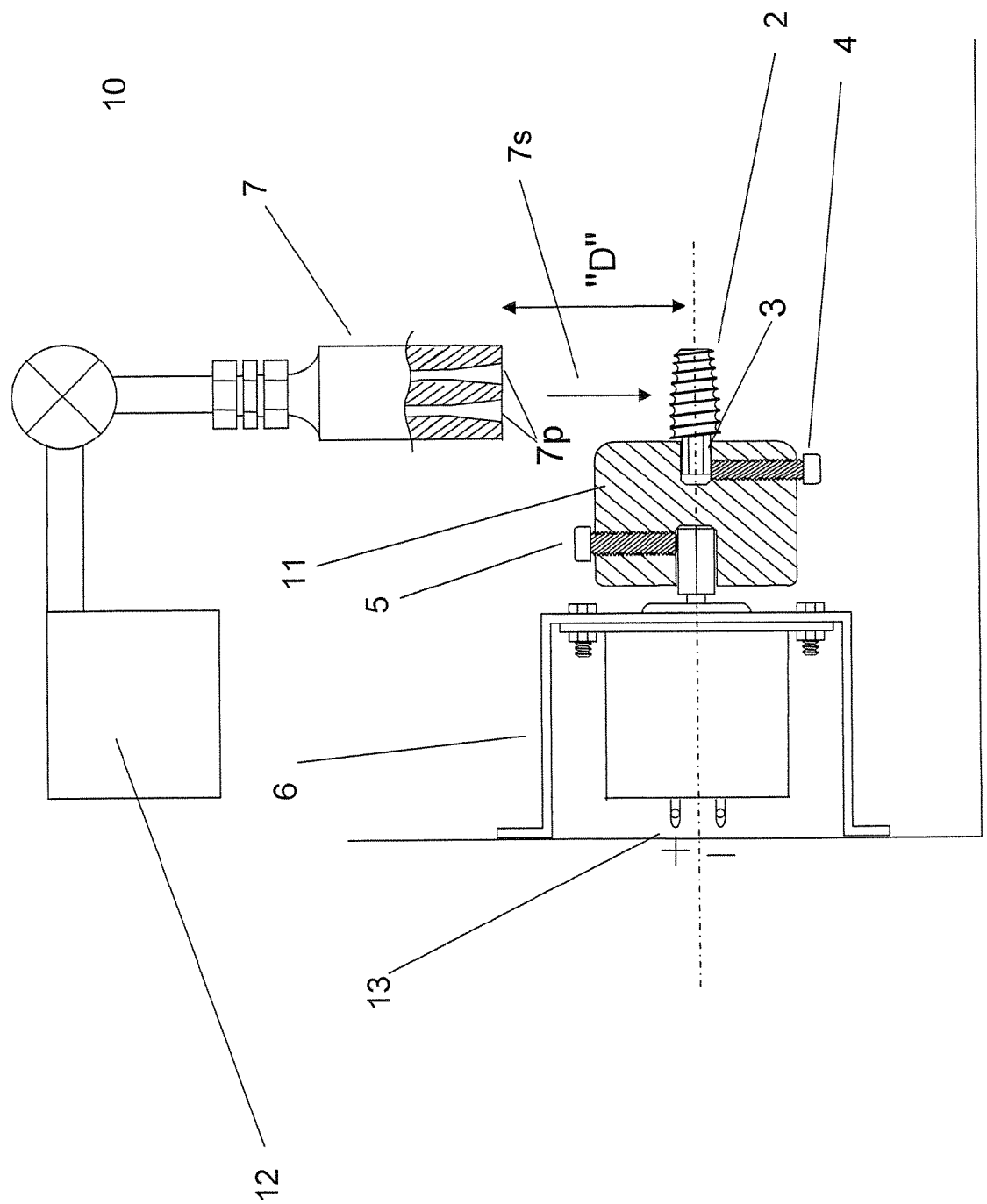
FIG. 1B is a schematic illustration of alternative configuration of the implant spin coater system, according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" refers to and encompasses any and all possible combinations of one or more of the associated listed items, as well as the lack of combinations when interpreted in the alternative ("or"). The term "about," as used herein when referring to a measurable value such as an amount of hydroxyapatite nanoparticles and the like, is meant to encompass variations of ±20%, ±10%, ±5%, ±1%, ±0.5%, or even ±0.1% of the specified amount. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

As used herein, the transitional phrase "consisting essentially of" means that the scope of a claim is to be interpreted to encompass the specified materials or steps recited in the claim, and those that do not materially affect the basic and novel characteristic(s) of the claimed invention. Thus, the term "consisting essentially of" when used in a claim of this invention is not intended to be interpreted to be equivalent to "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well known functions or constructions may not be described in detail for brevity and/or clarity.

All publications, patent applications, patents and other references cited herein are incorporated by reference in their entireties for the teachings relevant to the sentence and/or paragraph in which the reference is presented.

As used herein the phrase "liquid deposition technique" refers to any method of applying a liquid nanoparticle solution onto a surface of an implant. Examples of methods of applying the liquid solution include, but are not limited to, dipping the implant into a crystalline nanoparticle containing microemulsion, brushing, painting, and/or spraying the implant surface with the crystalline nanoparticle microemulsion, dropping, pouring, dripping, the crystalline nanoparticle solution onto the surface of the implant; and/or electrochemically applying the crystalline nanoparticle microemulsion to the implant surface.

As used herein the term "microtopography" refers to the micro structure of an implant surface, the implant surface having microscale irregularities. "Microscale" or "micro length scale" as used herein, refers to an article or feature generally measured in micrometers, for example, one to one hundred micrometers. As used herein, an implant surface microtopography includes surfaces having a rough finish and can include "rough" or "micro rough" and can include, but is not limited to, peaks, valleys, cracks and fissures.

The concept of surface roughness is a measure of the texture of a surface and is commonly used in general engineering practice. The most common value for measuring surface roughness is the Ra value. Ra is defined as the arithmetic average of the absolute values of the profile height deviations from the mean line, recorded within the evaluation length. This can be explained as taking the sum of the areas which are form when a mean line is drawn parallel to the surface in such as way that the areas are the same above and below the line. This summed area is then divided by the length of the sample length. The Ra value has the SI unit of m, but is usually given in micro meters or nano meters depending on the resolution of the measurements. Methods used to measure surface roughness include profilometers (dragging a measurement stylus across the surface), interferometry (an optical method) and various types of microscopy such as confocal microscopy, electron microscopy and atomic force microscopy.

As used herein, the phrase "proximate to" refers to next in time, order as in a series of events; next immediately preceding or following and/or a spatially close position.

Embodiments of the invention may be particularly suitable for surface modifications of medical implants for increasing the osseointegration of the implants. Some aspects of the embodiments of the invention include the deposition of a calcium phosphate nanoparticle layer onto the implant surface without altering of the implant roughness on the micrometer length scale (e.g., so that the implant substrate retains its original roughness and/or microtopography.

In some embodiments of the invention an implant spin coater system (10) is provided for applying crystalline nanoparticles onto the surface of an implant. Examples of such systems (10) are shown in FIGS. 1A and 1B. Thus, the implant spin coater system (10) of the present invention will be described in further detail with reference to FIGS. 1A and 1B. Accordingly, an embodiment of the present invention is a implant spin coater system (10) for applying crystalline nanoparticles onto the surface of an implant (2), to produce an implant (2) with a crystalline nanoparticle layer on its surface. The system (10) comprises a rotating or spin member (11); an implant holder (3) attached to the rotating member (11) configured to releasably hold a target implant (2); and optionally a pressurized gas supply (12) configured to direct a (pressurized) gas stream (7s) from the gas supply (12) toward the implant (2) typically in a direction that is substantially orthogonal to an implant (2) held by the implant holder (3). Thus, the implant (2) is placed in the implant holder (3) and secured with an attachment mechanism (4) such as a screw. The rotation member (11) can be placed and secured with another attachment mechanism (5) such as a screw onto the axle (8). The rotating member (11) can be an automated device with an electrical (DC) motor (6).

Figure 2:
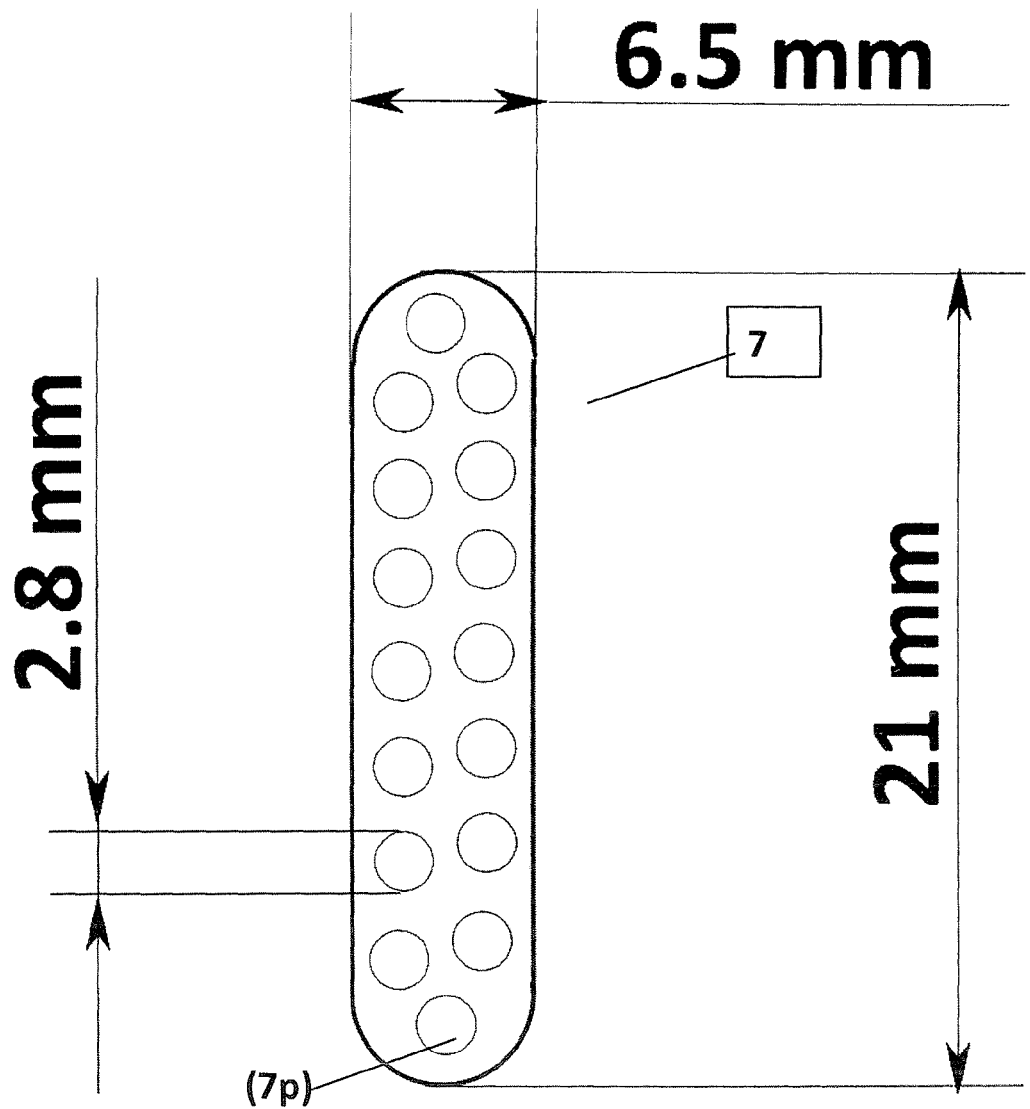
FIG. 2 is a schematic illustration of an exemplary gas nozzle used to direct and control a streaming gas flow over the implant surface, according to embodiments of the present invention.

In some embodiments, the gas supply (12) comprises at least one gas nozzle (7) for directing the gas stream (7s) at the implant. The gas nozzle (7) can be placed at a distance "D" from the implant (2) so that the whole implant (2) is subjected to the gas stream (7s) during the rotating or spinning step of the coating procedure. The size, spacing and amount of the flow ports (7p) in the nozzle (7), and also the number of nozzles can be different depending of the amount of gas flow desired at the surface of the implant and the size of the implant to be covered. As shown in FIG. 2, in some embodiments, the gas nozzle (7) has a length of about 21 mm and a width of about 6.5 mm and includes a plurality of flow ports (7p) that are spaced apart. The flow ports (7p) can have a diameter of between about 2 mm to about 3 mm, such as, for example a diameter of 2.8 mm. Other lengths and widths and port sizes can be used.

In some embodiments of the invention, the implant holder (3) releasably holds the implant (2) vertically or horizontally relative to the rotating member (11) and the position of the gas nozzle (7) (where used) is correspondingly adjusted to direct the gas stream (7s) in a direction that is substantially orthogonal to the implant (2). Thus, while FIG. 1A shows the implant in a vertical position with the gas nozzle (7) directed at it from the side, FIG. 1B shows that the implant can positioned at other angles. Thus, in some embodiments the implant (2) can be positioned horizontally with the nozzle (7) directed up or down so that the gas stream is directed substantially orthogonally to the implant (2). Further, the nozzle (7) can be placed at other angles and can be coupled with one or more additional nozzles positioned on both sides of the implant (2) or the nozzle (7) can be configured to circumferentially extend around the implant. In some embodiments, the gas stream can be pulsed in a coordinated manner with the rotating of the implant so that the thickness and uniformity of the layer of nanoparticles can be controlled.

The distance between the nozzle (7) and the implant (2) can differ depending of the amount of gas flow desired at the surface of implant. Thus, when used the gas nozzle is placed in a suitable position for directing a gas stream (7s) at the implant. In some embodiments, the gas nozzle (7) is placed so that the distance between the front edge of the nozzle (edge of the nozzle closest to the implant) and the center line of the implant is about 50 mm or less. In some embodiments, the distance between the center line of the implant to the front edge of the nozzle is about 30 mm. In some embodiments, the system (10) is configured so that the distance between the center line of the implant to the front edge of the nozzle is about 15 mm. However, it is contemplated that further and closer distances between the center line of the implant (2) to the front edge nozzle (7) can be used. The size and shape of the nozzle (7) can also vary depending on the size and shape of the implant so that the part of the implant that is to be coated is within the gas stream.

Figure 3:
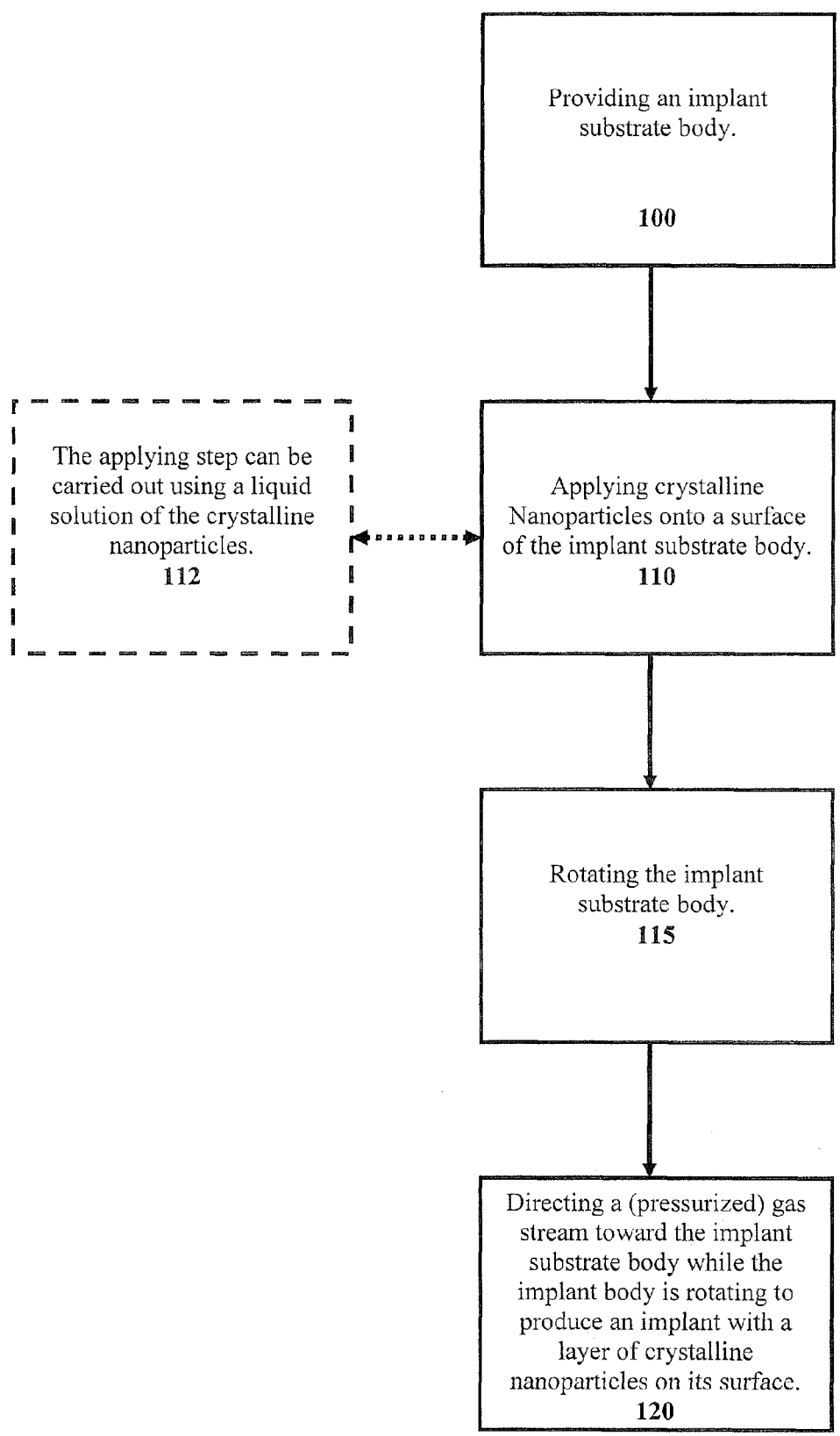
FIG. 3 is a flow chart of exemplary methods that can be used to prepare an implant with a nanoparticle layer on its surface according to some embodiments of the present invention.

FIG. 3 illustrates exemplary methods that can be used to prepare an implant with a nanoparticle layer on its surface according to some embodiments of the present invention. Accordingly, embodiments of the present invention are directed to methods of applying crystalline nanoparticles onto the surface of an implant to produce an implant with a crystalline nanoparticle layer on its surface. The methods including providing an implant substrate body (block 100); applying crystalline nanoparticles onto the surface of the implant substrate body (block 110); rotating the implant body (block 115); and optionally directing a gas stream toward the implant while the implant is rotating to produce an implant with a crystalline nanoparticle layer on its surface (block 120).

In some embodiments, the methods of the invention further comprise controlling the thickness of the crystalline nanoparticle layer and substantially retaining the microtopography of the implant surface in response to the applying, and rotating steps; and optionally the directing step. In further embodiments, the implant substrate body has a microtopography configuration.

In some embodiments, the implant surface microtopography has a rough surface with surface irregularities including, but not limited to, peaks and valleys having sizes between about 0.1 µm to about 500 µm. Thus, in some embodiments, the peaks and valleys have sizes between about 0.1 µm to about 400 µm, about 1.0 µm to about 400 µm, about 10 µm to about 300 µm, about 50 µm to about 250 µm, and the like.

Implants having various types of geometries can be modified with the described techniques. Thus, the implants of the present invention include, but are not limited to, any implant for medical use, typically human or veterinary use, including, but not limited to, joint implants such as hip implants, knee implants, shoulder implants and/or elbow implants; implant screws; dental implants; middle ear implants; and/or spinal implants, post amputation implants, hearing aid implants, facial implants, particular embodiments of the invention, the implant is an implant screw. In some embodiments, the implant is a dental implant with a post for affixing to local bone, the post may include a threaded (screw) head.

Also, the substrate material and/or chemical composition of the implant may vary. Accordingly, in some embodiments of the present invention, the implant body includes, but is not limited to, metal, ceramic, and/or combinations thereof. Exemplary metals include, but are not limited to metal such as titanium, stainless steel, cobalt, tantalum, chromium, yttrium, zirconium, aluminum, vanadium and/or alloys, and/or combinations thereof. Exemplary ceramics of the present invention include, but are not limited to, biocompatible ceramics such as zirconium oxide, titanium oxide, yttrium oxide, and/or aluminum oxide and/or combinations thereof. As discussed above, the implants may also be formed as combinations of metal and ceramic. Such metal/ceramic combinations include, but are not limited to, combinations of titanium and ceramic.

Exemplary crystalline nanoparticles include, but are not limited to, calcium phosphate nanoparticles, tricalcium phosphate, tetracalcium phosphate, octacalcium phosphate, carbonized HA, fluoro-apatite, magnesium doped apatite, strontium apatite, titanium oxide, yttrium oxide, zirconium oxide and/or combinations thereof. In particular embodiments, the calcium phosphate nanoparticles include, but are not limited to, HA nanoparticles. In some embodiments, the applying step can be carried out using a liquid solution of crystalline nanoparticles (block 112). According to some embodiments, the crystalline nanoparticles or nanocrystals can be applied as colloids of nanocrystals using a microemulsion solution. By definition, a microemulsion is a thermodynamically stable solution of oil, water and surfactants (sometimes also including a co-surfactant), which is typically substantially transparent and exhibits a low surface tension. Typical values for microemulsions are between 20 mN/m and 30 mN/m. Examples of microemulsions include water-in-oil microemulsions, oil-in-water microemulsions and bi-continuous microemulsions. Thus, in some particular embodiments, the microemulsion solutions can be one or more of water-in-oil microemulsions, oil-in-water microemulsions and bi-continuous microemulsions.

In particular embodiments, the microemulsions can be a water-in-oil microemulsion. A water-in-oil microemulsion comprises water droplets in a continuous oil phase that can be stabilized by a monolayer of surfactants. The microemulsions can have low surface tension and as a consequence, have a very high penetrability, meaning the microemulsion can penetrate small cavities of a solid, such as the implant surface microtopography. Furthermore, in some embodiments the microemulsions can form stable dispersions of nanoparticles, including, but not limited to, nanocrystalline HA. Surfactants, as used in the present invention, are amphiphilic molecules consisting of one or more hydrophilic part and one or more hydrophobic part. Any suitable surfactant known to one of skill in the art can be used with the microemulsions of the present invention. Exemplary surfactants include, but are not limited to, the nonionic surfactants of the type block-poly (ethylene glycol)-block-poly(propylene glycol-block (polyethylene glycol), fatty alcohol ethoxylate, fatty acid ethoxylate, fatty amide ethoxylate, fatty amine ethoxylate, alkylphenol ethoxylate and the anionic surfactants of the type alkyl carboxylate, alkyl ether carboxylate, alkyl sulfate, alkyl ethersulfate, alkylbenzene sulfonate, dialkylsulfosuccinate, alkyl phosphate, alkyl etherphosphate and the cationic of the type fatty amine salt, fatty diamine salt, alkyl quaternary ammonium salt, dialkyl quaternary ammonium salt and dialkyl ester quaternary ammonium salt or mixtures thereof.

In some embodiments, the nanoparticles, the nanoparticle dispersion, and/or the microemulsion comprising nanoparticles can be prepared from nanoparticles obtained as a dry powder. In other embodiments, the nanoparticles, the nanoparticle dispersion, and/or the microemulsion comprising nanoparticles can be prepared from nanoparticles obtained in a non-dry form.

In some embodiments, the crystalline calcium phosphate nanoparticles comprise crystalline HA nanoparticles. Accordingly, in some embodiments of the present invention, the nanocrystalline HA nanoparticles are produced in a liquid crystalline phase. In other embodiments, the methods of invention provide diluting the liquid crystalline phase comprising HA nanoparticles with at least one component of the liquid crystal to produce a microemulsion.

In further embodiments, the at least one component of the liquid crystal includes, but is not limited to, p-xylene and/or butylacetate. In still other embodiments, the microemulsion comprising the crystalline HA nanoparticles comprises a water-in-oil microemulsion. The range of concentrations for the crystalline hydroxyapatite nanoparticles in the liquid crystalline phase is 0.001%-50% dry weight.

In some embodiments, calcium phosphate nanocrystals can be manufactured according to a method described in PCT Patent Publication Number WO2005/123579. In the method of WO2005/123579, a liquid crystalline phase is used wherein the growth of the nanocrystalline calcium phosphate particles is hindered by the confined space of the liquid crystal. The formed nanoparticles are separated within the crystal and upon dilution with a non-water soluble component of the liquid crystal, the nanoparticle containing liquid crystalline phase is transformed into a water-in-oil microemulsion. In some embodiments, the non-water soluble component of the liquid crystal is p-xylene. In other embodiments, the non-water soluble component of the present invention includes, but is not limited to, p-xylene and other aromatic solvents, butylacetate and other alkylacetates, fatty alkane, fatty alkene, fatty alkyne, fatty alkane amide, cycloalkane, fatty alkylamine, alkane ester, fatty alkane nitril, fatty aldehyde, fatty ketone and fatty alcohol or mixtures thereof, and other components with similar water solubility.

In addition to calcium phosphate, the WO2005/123579 method can use, for example, also strontium apatite and/or fluoro-apatite.

In some embodiments, the calcium phosphate and/or HA nanocrystals can have a specific surface area in a range of between about 150 $m^2$/g to about 300 $m^2$/g. Thus, the specific surface area of the calcium phosphate and/or HA nanocrystals can be in a range from about 150 $m^2$/g to 200 $m^2$/g, from about 150 $m^2$/g to 250 $m^2$/g, from about 175 $m^2$/g to 200 $m^2$/g, from about 175 $m^2$/g to 250 $m^2$/g, from about 175 $m^2$/g to 275 $m^2$/g, from about 175 $m^2$/g to 300 $m^2$/g, from about 200 $m^2$/g to 250 $m^2$/g, from about 200 $m^2$/g to 275 $m^2$/g, from about 200 $m^2$/g to 300 $m^2$/g, from about 250 $m^2$/g to 275 $m^2$/g, from about 250 $m^2$/g to 300 $m^2$/g, from about 275 $m^2$/g to 300 $m^2$/g, and the like.

In some embodiments, the HA nanocrystals can have a diameter in a range of between about 1 nm to about 20 nm (average size). In some embodiments, the HA nanocrystals can have a diameter in a range of between about 2 nm to about 20 nm (average size). In particular embodiments, the diameter of the HA nanocrystals can be in a range of between about 1 nm to about 5 nm in diameter on average. The length of the HA nanocrystals can be between about 20 nm to about 200 nm. In some embodiments, the length of the HA nanocrystals can be in a range from about 20 nm to about 100 nm, from about 50 nm to about 100 nm, from about 50 nm to about 200 nm, from about 100 nm to about 200 nm, from about 150 nm to about 200 nm, and the like. In particular embodiments, the calcium to phosphor ratio of the crystalline calcium phosphate nanoparticles can be in a range from about 1.0 to about 2.5. In some particular embodiments the calcium to phosphor ratio of the crystalline calcium phosphate nanoparticles can be about 1.67.

As discussed above, embodiments of the present invention provides a method of applying crystalline nanoparticles onto the surface of an implant to produce an implant with a crystalline nanoparticle layer on its surface. Accordingly, in some aspects of the invention, the applying step comprises the applying the crystalline nanoparticles to the implant surface as a liquid microemulsion and other liquid forms in which the nanoparticles can be dispersed.

In particular embodiments, the applying step includes at least one of the following: (a) dipping the implant into a crystalline nanoparticle liquid microemulsion; (b) spraying the implant surface with the crystalline nanoparticle microemulsion; (c) dripping the crystalline nanoparticle microemulsion onto the implant surface; or (d) pouring the crystalline nanoparticle microemulsion onto the surface of the implant.

In some embodiments, prior to the applying step, the implant surface can be generally cleaned and dried to allow a strong adhesion of the nanoparticles. Any technique known by one of skill in the art for this purpose can be used. Such techniques include, but are not limited to, mechanical techniques including, but not limited to, shot-peening, blasting and polishing, and chemical techniques, including, but not limited to, washing with any suitable materials such as organic solvents, acids, bases, surfactants or water. In some embodiments, there is no other pre-treatment of the implant required prior to applying the liquid nanoparticle solution.

In some embodiments, the implant can be rotated at a selected rotation speed typically in a range from between about 500 rotations per minute (rpm) to about 10,000 rpm. Thus, rotational speeds of the invention can be in a range from about 500 rpm to about 7500 rpm, including for example, from about, from about 2000 rpm to about 5000 rpm, and the like. In some embodiments, the rotational speed is about 2250 rpm. In other embodiments the rotational speed is about 3500 rpm. In still other embodiments, the rotational speed is about 4700 rpm. A further aspect of the invention provides a method wherein the liquid solution can be applied to the implant before the implant is loaded onto the rotation member or mandrel. In another embodiment, the applying step can be carried out during the rotating step. In other embodiments, the liquid solution of nanoparticles can be applied to the implant before and during the rotating of the implant.

As discussed above, in some embodiments, a gas stream can be directed to flow toward the implant while it is rotating. In some embodiments, the gas stream directed toward the implant comprises a non-reacting gas. A non-reacting gas includes any gas that does not react with the implant surface. Such non-reacting gases include, but are not limited to, air, nitrogen and/or argon. Thus, in some embodiments, as shown in FIGS. 1A and 1B, a gas stream (7s) can be directed at the implant. The gas stream comprises a non-reacting gas comprising at least one of the following: (a) air; (b) nitrogen; (c) argon; (d) helium or other noble gases.

The gas can be supplied from a pressurized gas supply (12). The flow path can include flow meters, valves and filters to filter any undesired impurities (such as liquid).

The flow rate of the gas stream can be in a range of between about 1 L/min to about 200 L/min. Thus, the gas stream flow rate can be about 1 L/min, 10 L/min., 20 L/min, 30 L/min, 40 L/min, 50 L/min, 60 L/min, 70 L/min, 80 L/min, 90 L/min, 100 L/min, 110 L/min, 120 L/min, 130 L/min, 140 L/min, 150 L/min, 160 L/min, 180 L/min, 190 L/min, 200 L/min, and the like. The gas stream flow rate can be in a range from between about 1 L/min to about 100 L/min, about 10 L/min to about 100 L/min, about 10 L/min to about 200 L/min, about 40 L/min to about 80 L/min, about 50 L/min to about 100 L/min, about 50 L/min to about 150 L/min, about 100 L/min to about 200 L/min, and the like. In some embodiments, the gas stream flow rate is about 40 L/min, while in other embodiments, the gas stream flow rate can be about 80 L/min. In some embodiments, the implants can be actively or passively dried after the liquid microemulsion is applied and the implant is rotated for a desired time. In some embodiments, the temperature of the drying is carried out at room temperature. In other embodiments, the drying is carried out using a heater. In some embodiments, the implant can be dried before the implant is heated. In some embodiments, the drying step is carried out at the heating step to form a nanoparticle layer.

In some embodiments, the implant can be heated to a temperature sufficient to substantially or completely remove any remaining surfactant. In some embodiments, the heating step is carried out in an oven with a gaseous atmosphere. Examples of gaseous atmospheres include, but are not limited to, oxygen, nitrogen, argon, air, and any combination thereof. The temperature for the heating step can vary with the type of gaseous environment, the type of surfactant used and the length of time of the heating step. Thus, the temperature for the heating step can be in a range from about 250° C. to about 700° C. In some embodiments, an implant is heated for about 5 min, at about 550° C. in oxygen. Determination of the appropriate temperature would be routine in the art based on the factors identified in the present disclosure.

Additional layers of the nanocrystalline material can be formed by repeating the above steps, e.g., the applying and rotating steps, and optionally the directing step, are repeated at least once after the drying and/or heating steps. Additional applying and rotating steps; and optionally, the directing step, increases the nanoparticle layer, and can thereby be used as a tool for controlling the thickness of the nanoparticle layer on the surface of the implant.

As mentioned above, in some embodiments, the thickness of the crystalline nanoparticle layer can be controlled and the microtopography of the implant surface can be substantially retained in response to the applying and rotating steps; and optionally, the directing step. More particularly, in some embodiments, controlling the thickness of the nanoparticle layer on the surface of the implant comprises at least one of the following: (a) the rotational speed of the implant; (b) the concentration of the crystalline nanoparticle solution; or (c) the rate of flow and pressure of the gas stream.

Figure 5:
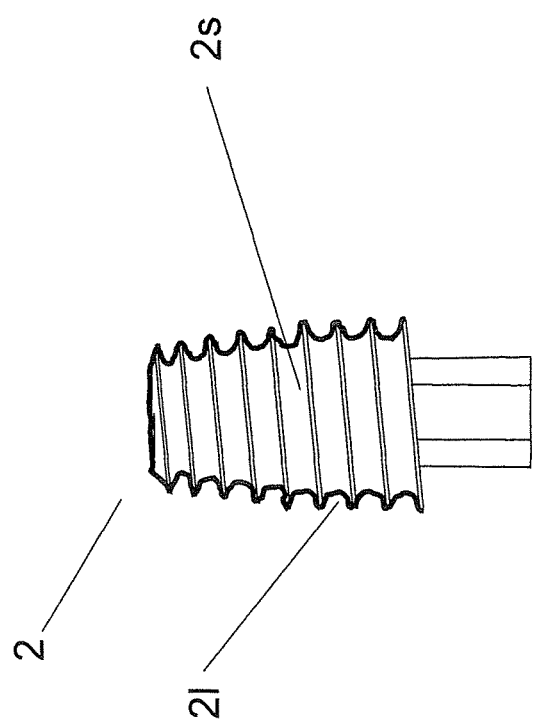
FIG. 5 is a schematic illustration of an exemplary dental implant according to embodiments of the present invention.

In some embodiments, as shown in FIG. 5, the nanoparticle layer (21) on the surface of the implant (2) has a thickness in a range from between about 2 nanometer to about 500 nanometers. As discussed above, the implant surface may be microrough and thus have irregularities in the micrometer length scale. As discussed above, in some embodiments, the micrometer sized irregularities are substantially retained when using the methods of the present invention.

Thus, in some embodiments, the thickness of the nanoparticle layer applied to the implant surface may be affected by the particle concentration of the nanoparticles or nanoparticle microemulsion used in the applying step. In general, a higher concentration results in a higher amount of deposited particles, and hence, a thicker layer of nanoparticles on the implant surface. Conversely, a lower nanoparticle concentration results in a reduced amount of the adhered particles, and as a consequence a thinner layer. In some embodiments, thickness of the nanoparticle layer can also be affected by and/or controlled by the spinning or rotational speed, which is measured in revolutions per minute (RPM). In some embodiments, the thickness of the nanoparticle layer can be affected by and/or controlled by the rate of gas flow, measured in liters·min$^{-1}$ (L/min), of a gas onto the implant through a defined nozzle (see, for example, FIG. 2). Generally, an increased speed of rotation results in a thinner nanoparticle layer since the centrifugal force is increased with the speed. However, the effect of directing a gas stream toward the implant is also dependent on the rotational speed of the implant, especially in regard to the homogeneousity of the resulting layer of nanoparticles. As a consequence, an increased rotational speed in combination with the flow rate/pressure of the gas stream (7s) toward the implant (2) may, in some cases, increase the thickness of the nanoparticle layer. Furthermore, at a specific rotational speed, the thickness of the nanoparticle layer decreases with an increased rate of gas flow. Thus, a well defined layer of a nanoparticles can be formed on the surface of the implant in which the implant surface is well covered and the micro roughness is substantially retained or not changed at all, based on the rotation or spin rate and the blowing or gas stream flow rate.

Accordingly, as shown in FIG. 5, in some embodiments of the present invention, the implant (2) can have a nanoparticle layer (2L) on the surface of the implant that is in a range of between about 2 nm to about 500 nm. Thus, the nanoparticle layer can be in a range of between about 2 nm to about 10 nm, from about 2 nm to about 50 nm, from about 2 nm to about 100 nm, from about 2 nm to about 200 nm, from about 2 nm to about 300 nm, from about 2 nm to about 400 nm, from about 10 nm to about 50 nm, from about 10 nm to about 100 nm, from about 10 nm to about 200 nm, from about 10 nm to about 300 nm, from about 10 nm to about 400 nm, from 10 to about 500 nm, from about 50 to about 100 nm, from about 50 nm to about 200 nm, from about 50 nm to about 300 nm, from about 50 nm to about 400 nm, from 50 to about 500 nm, from about 100 nm to about 200 nm, from about 100 nm to about 300 nm, from about 100 nm to about 400 nm, from about 100 nm to about 500 nm, from about 200 nm to about 300 nm, from about 200 nm to about 400 nm, from about 200 nm to about 500 nm, from about 300 nm to about 400 nm, from about 300 nm to about 500 nm, from about 400 nm to about 500 nm, and the like.

In particular embodiments, the implant (2) is a dental implant, as shown in FIG. 5. In some embodiments, the nanoparticles comprise HA nanoparticles. The dental implant can be comprised of metal or ceramic. In still further embodiments, the dental implant comprises one of the following metals: (a) titanium; (b) tantalum; (c) stainless steel; (d) chromium; (e) cobalt; (f) alloys thereof, or combinations thereof. In other embodiments, the implant comprises ceramic which further comprises one of the following: (a) zirconium oxide; or (b) aluminum oxide. In other embodiments, the dental implant comprises titanium. In still other embodiments, the dental implant comprises a combination of metal and ceramic. In another aspect, the crystalline nanoparticle layer on the surface of the dental implant comprises a thickness in a range from about 2 nm to about 500 nm. Thus, the nanoparticle layer can be in the ranges as set forth above. In yet other embodiments, the microtopography of the implant with a crystalline nanoparticle layer on its surface is substantially retained.

In a particular embodiments, a dental implant (2) (FIG. 5) is titanium with a nanocrystalline hydroxyapatite nanoparticle layer applied to its surface, the thickness of the layer being in a range of between about 2 nm to about 500 nm. The microtopography of the dental implant surface is substantially retained, and the nanocrystalline hydroxyapatite nanoparticle layer is stoichimetric and in a crystalline form.

The dental implants of the present invention can be used, for example, as artificial tooth replacements. In some embodiments, the dental implant (2) has a screw portion (2s) (FIG. 5) that is titanium and that has been pretreated by shot-peening, blasting and/or acid-etching, which creates a high surface roughness on the micrometer length scale. Thus, the microtopography of the titanium screw is micro rough. As discussed above, having a micro rough microtopography can be a desired property because it can promote osseointegration, thus enhancing the implant's ability to adhere to bone tissue.

Figure 4:
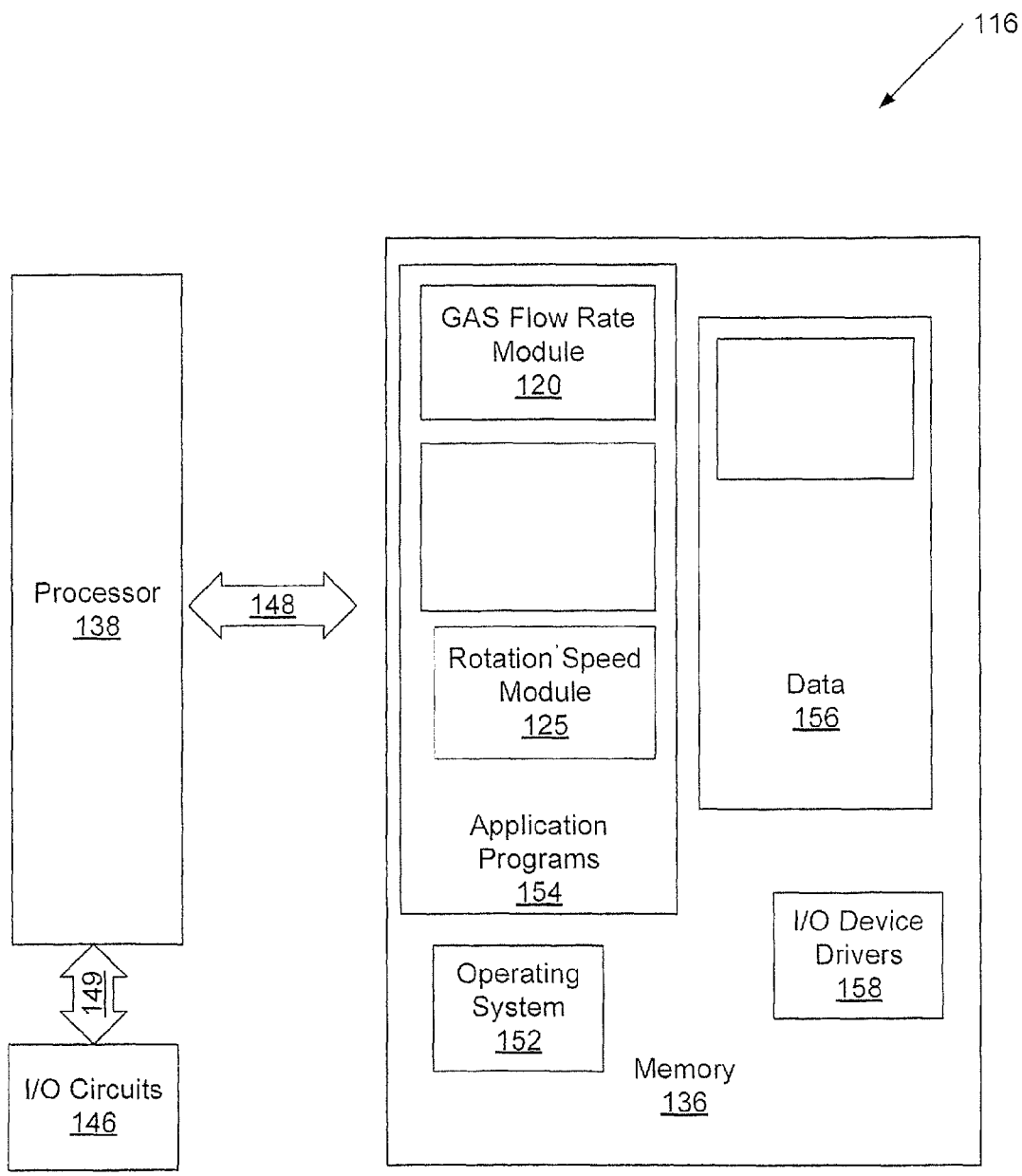
FIG. 4 is an exemplary data processing system that may be included in devices operating in accordance with some embodiments of the present invention

The spin coater system (10) can be automated or semi-automated and can also be provided with a controller configured to control the rotation speed of the rotating member and the flow rate of the gas stream. Thus, FIG. 4 illustrates an exemplary data processing system or database environment for a controller that may be included in devices operating in accordance with some embodiments of the present invention. The input/output circuits 146 can be used to transfer information between the memory (memory and/or storage media) 136 and another computer system or a network using, for example, an Internet protocol (IP) connection using conventional components such as those used in many conventional data processing systems to control the rotational speed and/or gas flow and/or to allow a user to adjust or select those operating parameters using an HMI (Human Machine Interface) or other UI (User Interface).

The present invention is more particularly described in the Examples set forth below, which are not intended to be limiting of the embodiments of this invention.

EXAMPLES

The surface of the implant, the nanoparticle surface coverage and the amount of deposited HA nanocrystals have been evaluated using Field Emission Scanning Electron Microscopy (FESEM), X-Ray Photoelectron Spectroscopy (XPS) and Atomic Emission Spectroscopy (AES). The FESEM and XPS were performed on the samples without any pretreatment of the specimen. For the AES analysis, the coated implants were placed in nitric acid (1.6 ml of 0.8 ml 65% $HNO_3$ and 0.8 ml water) for 20 min to dissolve all HA on the surface. The solution is then diluted with 20 g water.

Example 1

Influence of the Rotational Speed

The thickness/surface coverage of hydroxyapatite nanocrystals layer on implants, in this particular case having a dental screw design, as a function of various rotational speeds was estimated using XPS and FESEM. The coating procedure used in this example was; 1) the implant (2) was placed, standing up (vertical), in an implant holder (3) depicted in FIG. 1A, 2) the coating solution, comprised of a microemulsion containing the hydroxyapatite nanoparticles, was applied to the implant so that the whole implant surface was covered, 3) the implant was rotated, at various speeds as described in this example, 4) after the implant was allowed to dry at room temperature, it was heat treated, in this particular example at 550° C. for 5 minutes in an oxygen atmosphere, 5) after the implant cooled to room temperature, steps 1-4 were repeated one time.

Using XPS, the combined amounts of calcium, Ca, and phosphorous, P, as well as titanium, Ti, were determined for the implants after the coating procedure described in this example had been performed. By dividing the total amount of Ca and P with the amount of Ti on the surface, an indication of the layer's surface coverage can be calculated. When implants were rotated with a rotational speed of 2250 rpm, 3500 rpm and 4700 rpm, the total amount of Ca and P divided by the surface amount of Ti was 46.6, 40.9 and 17.9, respectively. The decrease of Ca and P compared to Ti when increasing the rotational speed indicates a lower surface coverage of hydroxyapatite on the implant surface. All XPS results are also presented in Table 1.

TABLE 1

| Figure | Rotational speed (rpm) | Nitrogen flow rate (Lmin$^{-1}$) | Tot. amount CaP (%) | Amount of Ti (%) | Coverage (CaP/Ti) |
| --- | --- | --- | --- | --- | --- |
| 6B | 2250 | 0 | 32.6 | 0.7 | 46.6 |
| 6C | 2250 | 40 | 27 | 2.2 | 12.3 |
| 6D | 2250 | 80 | 29.9 | 3.1 | 9.6 |
| 6E | 3500 | 0 | 32.7 | 0.8 | 40.9 |
| 6F | 3500 | 40 | 30.4 | 2 | 15.2 |
| 6G | 3500 | 80 | 30.2 | 2.4 | 12.6 |
| 6H | 4700 | 0 | 32.3 | 1.8 | 17.9 |
| 6I | 4700 | 40 | 31.6 | 2.1 | 15 |
| 6J | 4700 | 80 | 29.3 | 3.3 | 8.9 |
| 6K | 3500 | 40 | 29.1 | 4.0 | 7.3 |
| 6L | 3500 | 40 | 26.4 | 5.7 | 4.6 |

However, when comparing FESEM images, see FIGS. 3A, 3B, 3E and 3H, it can be seen that much of the implant surface micro roughness has been covered by the hydroxyapatite layer producing a smoother appearance and that the initial unmodified implant surface has been completely covered.

The dissolved HA layer on the implant surface was analyzed with AES and compared with an implant which had not been spun after the addition of coating solution. The total amount of Ca and P was 1.11 mg/L, 0.58 mg/L, 0.49 mg/L and 0.52 mg/L, when the implants were not spun, or spun with a speed of 2250 rpm, 3500 rpm or 4700 rpm, respectively.

Example 2

Influence of Directing a Gas Stream

Using XPS and FESEM, the amount or surface coverage of hydroxyapatite on implants, in this particular case having a dental screw design was estimated as a function of various rotational speeds and whether a gas stream directed towards the implant was used during this step. The coating procedure used in this example was; 1) the implant (2) was placed, standing up (vertically), in an implant holder (3) depicted in FIG. 1A, 2) the coating solution, comprised of a microemulsion containing the hydroxyapatite nanoparticles, was applied to the implant so that the whole implant surface was covered, 3) the implant was rotated, at various speeds as described in this example, with and without streaming nitrogen gas through a nozzle (7) as depicted in FIGS. 1A and 1B, at different nitrogen flow rates as described in this example, 4) after the implant was allowed to dry at room temperature, it was heat treated, in this particular example at 550° C. for 5 minutes in an oxygen atmosphere, 5) after the implant cooled to room temperature steps 1-4 was repeated one time.

Using XPS, the combined amounts of Ca and P as well as Ti, were determined for the implants after the coating procedure described in this example had been performed. By dividing the total amount of Ca and P with the amount of Ti on the surface, an indication of the layer's surface coverage can be calculated. When an implant was rotated with a rotational speed of 2250 rpm without streaming nitrogen gas over the implant during step 3 of the coating procedure as described in this example, a total amount of Ca and P compared to Ti was 46.6. When compared to an implant that in step 3 that included streaming nitrogen gas over the implant with nitrogen flow rates of 40 L/min and 80 L/min, the total amount of Ca and P compared to Ti was decreased to 12.3 and 9.6, respectively. Since the total amount of Ca and P compared to Ti decreases on the implant surface when streaming nitrogen gas over the implant while rotating, these results indicate that streaming nitrogen gas while rotating decreases the amount of HA on the implant surface. The same relationships are seen when increasing the rotational speed. At 3500 rpm, the total amount of Ca and P compared to Ti was 40.9, 15.2 and 12.6 with no streaming nitrogen gas, with streaming nitrogen gas at a flow rate of 40 L/min and 80 L/min, respectively. At 4700 rpm the total amount of Ca and P compared to Ti was 17.9, 15.0 and 8.9 with no streaming nitrogen gas, with streaming nitrogen gas at flow rates of 40 L/min and 80 L/min, respectively. All XPS results are also presented in Table 1.

FESEM images of the same implants analyzed with XPS are shown in FIG. 6A-6J. From these images it can be clearly seen that the amount of HA nanocrystals decreases when streaming nitrogen gas is used while rotating the implant. Also, it is clear the topography is strongly affected by streaming nitrogen gas over the implant surface. When the implant is rotated without streaming nitrogen gas, the implant's surface micro roughness is covered by the HA nanocrystals forming a smoother appearance. When the implant is both rotated and nitrogen gas is streamed over the implant the thinner HA nanocrystal layer follows the underlying surface and thereby maintains the implant's surface micro roughness.

By optimizing the rotational speed and the nitrogen flow rate, the HA nanocrystal layer can be adapted to closely follow the implant surface micro roughness. Also, when spinning without blowing, buildups of HA layer can form around larger structures on the implant, such as threads. This can be seen in FIGS. 6M and 6N where the dark areas on both side of the thread are an indication of a thicker layer which completely covers the underlying micro roughness. When applying nitrogen gas while rotating, however, these dark areas are removed.

The dissolved HA layer on the implant surface was analyzed with AES. When the implant was rotated with a rotational speed of 2250 rpm without streaming nitrogen gas over the implant during step 3 of the coating procedure as described in this example the amount of Ca and P was 0.58 mg/L. The amount of Ca and P of implants, which included streaming nitrogen gas as described in the coating procedure in this example with a flow of 40 L/min and 80 L/min, was 0.78 and 0.61 mg/l, respectively. When the implant was rotated with a rotational speed of 3500 rpm without streaming nitrogen gas, with streaming nitrogen gas at flow rates of 40 L/min and 80 L/min as described in this example's coating procedure, the amount of Ca and P were 0.49 mg/L, 0.83 mg/L and 0.66 mg/L, respectively. When the implant was rotated at a speed of 4700 rpm without streaming nitrogen gas, with streaming nitrogen gas at a flow rate of 40 L/min and 80 L/min as described in this example's coating procedure, the amount of Ca and P was 0.52 mg/L, 0.54 mg/L and 0.80 mg/L, respectively.

Example 3

Influence of the Number of Coatings

According to the two above described examples the coating procedure is performed twice per implant to produce the hydroxyapatite layer. In this particular example the coating procedure is terminated after the first heat treatment; 1) the implant (2) was placed, standing up (vertical), in an implant holder (3) depicted in FIG. 1A, 2) the coating solution, comprised of a microemulsion containing the hydroxyapatite nanoparticles, was applied to the implant so that the whole implant surface was covered, 3) the implant was rotated at various speeds, as described in this example, with streaming nitrogen gas over the implant surface with a nozzle (7) depicted in FIG. 2, using a gas flow of 40 L/min, 4) after the implant was allowed to dry at room temperature, it was heat treated, in this particular example for at 550° C. for 5 minutes in a oxygen atmosphere.

From measurements using XPS and FESEM, an implant coated according to the coating procedure described in this example was compared to an implant coated according to the coating procedure described in Example 2. The rotational speed used in this example for the implants was 3500 rpm with a nitrogen flow rate of 40 L/min.

Using XPS, the combined amount of Ca and P as well as Ti was determined for the implants after the coating procedure described in this example had been performed. By dividing the total amount of Ca and P with the amount of Ti on the surface, an indication of the layer's surface coverage can be calculated. The total amount of Ca and P compared to Ti on the implant surface was 7.3, for an implant following the coating procedure described in this example. For an implant coated according to Example 2 with the same rotational speed and nitrogen flow rate as for the implant coated as described in this example, the total amount of Ca and P compared to Ti on the implant surface was 15.2. When coating with only one layer as described in this example, it is clear that the total amount of Ca and P compare to Ti is decreased by approximately 50% compared to when the implant was coated twice. This indicates the presence of a thinner layer. All XPS results are also presented in table 1.

From the FESEM images, see FIGS. 6F and 6K, it can be seen that a thinner layer is present on the implant surface which only was coated once, as described in this example.

The dissolved HA layer on the implant surface was analyzed with AES. For the implant following the procedure described in this example, the total amount of Ca and P was 0.57 mg/L. If an implant is coated as described in example 2, (rotational speed of 3500 rpm and nitrogen flow rate of 40 L/min), the total amount of Ca and P was 0.83 mg/L. With only one coating, as described in this example, the amount of Ca and P is 31% less than when two coatings, as described in example 2, are used. This shows that the thickness of the Ca and P layer can be controlled by the number of coating performed on the implant surface.

Example 4

Influence of the Particle Concentration

An implant coated according to Example 2, (rotational speed of 3500 rpm and nitrogen flow rate of 40 L/min), was compared to an implant coated according to the coating procedure described in Example 2 with a coating solution containing 50% of the concentration of the hydroxyapatite nanocrystals used in Example 2.

The two implants were compared using XPS and FESEM. All XPS results are also presented in table 1. Using XPS, the combined amount of Ca and P as well as Ti was determined for the implants after the coating procedure described in this example had been performed. By dividing the total amount of Ca and P with the amount of Ti on the surface an indication of the layer's surface, coverage can be calculated. The total amount of Ca and P compared to the amount of Ti on the implant surface coated as described in Example 2, (rotational speed of 3500 rpm and nitrogen flow rate of 40 L/min), was 15.2. For an implant coated as described in Example 2 but with a coating solution containing 50% of HA nanocrystals compared to the coating solution in Example 2, the total amount of Ca and P compared to Ti on the surface was 4.6. From the FESEM images, see FIGS. 6F and 6L, it can be seen that a thinner layer is present on the implant surface which was coated with a solution containing 50% of the nanocrystal concentration, as described in this example.

The dissolved HA layer on the implant surface was analyzed with AES. The total amount of Ca and P on the implant surface, coated as described in Example 2 (rotational speed of 3500 rpm and nitrogen flow rate of 40 L/min), was 0.83 mg/L. For an implant coated as described in Example 2, but with a coating solution containing 50% of HA nanocrystals compared to the coating solution in Example 2, the total amount of Ca and P was 0.39 mg/L, which is in direct correlation to the particle concentration of the microemulsion coating solutions. Thus, lower nanoparticle concentration can be utilized to further increase the control of the thickness of the Ca and P layer.

Example 5

Exemplary Method for Producing a Hydroxyapatite Nanoparticle Coated Implant Surface Preserving the Micro Roughness of the Implant.

The procedure to produce the implants was; 1) the implant (2) was placed, standing up (vertical), in an implant holder (3) depicted in FIG. 1A, 2) the coating solution, comprised of a microemulsion containing the hydroxyapatite nanoparticles, was applied to the implant so that the whole implant surface was covered, 3) the implant was rotated with 3500 rpm with streaming nitrogen gas through a nozzle (7) depicted in FIG. 2, at a nitrogen flow rate of 40 L/min, 4) after the implant was allowed to dry at room temperature, it was heat treated at 550° C. for 5 minutes in an oxygen atmosphere, 5) after the implant cooled to room temperature, steps 1-4 were repeated one time.

Example 6

Animal Study

Figure 7:
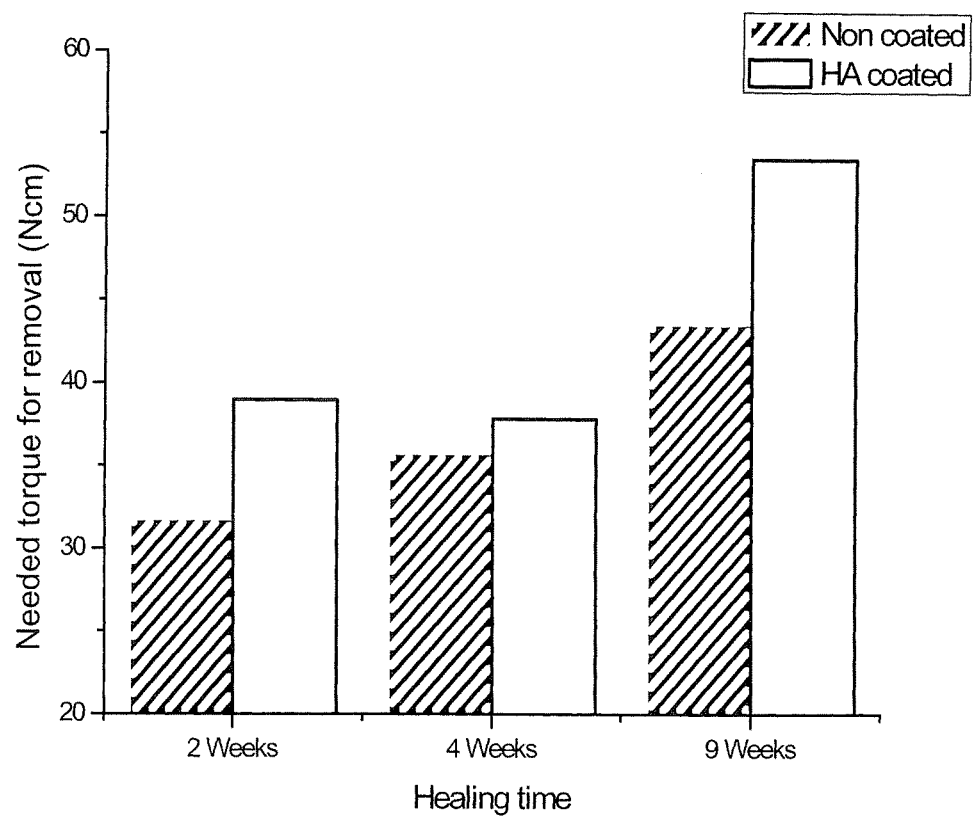
FIG. 7 is a graph of removal torque (Ncm) versus healing time (weeks) for non-coated and HA coated implants, showing results from an animal study with the torque needed for removal of the implants' removal as a function of different healing times.

An animal study was performed to study the effect of the nanocrystalline hydroxyapatite coating. In the study, the osseointegration of titanium implants without coating and coated two times, according to example 5, were compared at three different healing times (2, 4, and 9 weeks). 30 adult New Zealand White female rabbits were used in this study, which was approved by the local ethical committee at Gothenburg University. All animals were 9 months old and had two implants inserted in each leg in the proximal tibia methaphysis. The animals were anaesthetized with intramuscular injections of fentanyl 0.3 mg/ml and fluanisone 10 mg/ml, (Hypnorm Vet, Janssen Pharmaucetica, Beerse, Belgium) at a dose of 0.5 ml/kg of body weight and intraperitoneal injections of diazepam (Stesolid Novum, Dumex Alpharma, Denmark) at a dose of 2.5 mg per animal. If necessary, anaesthesia was maintained using additional doses of fentanyl and fluanison at a dose of 0.1 ml/kg body weight. Before surgery, 1.0 ml of lidocaine (Xylocain, Astra Zeneca, Sweden) was administered subcutaneously in the intended surgical sites. The experimental sites were opened via incisions through skin and fascia, and the bone surfaces exposed with the aid of an elevator. The implants were placed after preparation with guide and twist drills of 2.0 and 3.2 mm in diameter. During all surgical drilling sequences, low rotatory speed with profuse saline cooling was used. The wounds were closed by suturing the fascia and skin separately. The animals were kept in separate cages and immediately after surgery they were allowed to run freely. The follow-up time was 2, 4 and 9 weeks and the animals were sacrificed with an overdose of pentobarbital (60 mg/ml) (Pentobarbitalnatrium, Apoteksbolaget, Sweden). The biomechanical test of the implant-bone interface was performed with the removal torque (RTQ) test. The RTQ instrument was an electronic equipment (Detektor AB, Gothenburg, Sweden) involving a strain gauge transducer used for testing the implant stability (the peak loosening torque in Ncm). A linearly increasing torque is applied on the same axis of the implant until failure of integration was reached, and the peak value recorded. The results are presented in FIG. 7 and clearly shows that a higher torque of removal was needed for the HA coated implants in comparison with the non coated ones. The values were 23% higher after 2 weeks, 6% higher after 4 weeks and 23% higher after 9 weeks.

Example 7

The surface roughness, Ra, was measured using a profilometer on the implants that were used in example 6 and which are presented in FIG. 6. The implants were measured before and after the deposition of the nanoparticles. The Ra values were found to be 1±0.1 μm (the variations were between the different implant samples) and did not change after the deposition of the nanoparticles. This clearly shows that the described method retains the underlying micro roughness of the implant surface.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of applying crystalline nanoparticles onto the surface of an implant to produce an implant having a crystalline nanoparticle layer with a controlled thickness on its surface, the method comprising:
    providing an implant substrate body;
    applying a liquid dispersion of crystalline nanoparticles onto the surface of the implant substrate body;
    rotating the implant substrate body;
    directing a pressurized gas stream toward the implant while the implant is rotating to remove excess crystalline nanoparticles to form a crystalline nanoparticle layer with a controlled thickness in a nanometer range on the surface of the implant.

2. The method of claim 1, wherein providing the implant substrate body comprises providing an implant substrate body comprising microtopography on its surface.

3. The method of claim 2, further comprising controlling the thickness of the crystalline nanoparticle layer and substantially retaining the microtopography of the implant surface in response to the applying and rotating steps.

4. The method of claim 2, wherein the microtopography of the implant surface is micro-rough.

5. The method of claim 1, wherein the applying occurs before, during or before and during the rotating step.

6. The method of claim 1, wherein the directing comprises a gas stream at a flow rate between about 40 l/min to about 80 l/min toward the implant.

7. The method of claim 1, wherein the gas stream comprises a non-reacting gas comprising at least one of the following: (a) air; (b) nitrogen; or (c) argon.

8. The method of claim 1, wherein the liquid dispersion containing the crystalline nanoparticles is a microemulsion.

9. The method of claim 8, further comprising heating the implant in a gaseous atmosphere after the applying and rotating steps, wherein the microemulsion comprises a surfactant and the heating is to a temperature sufficient to substantially or completely remove any remaining surfactant, whereby the implant has a dried outer coating of crystalline nanoparticles.

10. The method of claim 9, comprising repeating the applying and rotating steps at least once after the heating step to apply at least one additional layer of crystalline nanoparticles.

11. The method of claim 1, wherein the thickness of the nanoparticle layer on the surface of the implant is controlled by at least one of the following: (a) the rotational speed of the implant; (b) the concentration of the crystalline nanoparticles; or (c) the rate of flow of the gas stream.

12. The method of claim 1, wherein the crystalline nanoparticles comprise calcium phosphate nanoparticles.

13. The method of claim 12, wherein the calcium phosphate nanoparticles comprise nanocrystalline hydroxyapatite nanoparticles.

14. The method of claim 13, wherein the nanocrystalline hydroxyapatite nanoparticles comprise a surface area in the range of about 150 $m^2/g$ to about 300 $m^2/g$.

15. The method of claim 1, wherein the applying step comprises at least one of the following: (a) dipping the implant into the crystalline nanoparticle liquid dispersion; (b) spraying the implant surface with the crystalline nanoparticle liquid dispersion; (c) dripping the crystalline nanoparticle liquid dispersion onto the implant surface; or (d) pouring the crystalline nanoparticle liquid dispersion onto the surface of the implant.

16. The method of claim 1, wherein the implant comprises metal or ceramic.

17. The method of claim 16, wherein the implant comprises at least one of the following metals: (a) titanium; (b) tantalum; (c) stainless steel; (d) chromium; (e) cobalt; (f) alloys thereof; or combinations thereof.

18. The method of claim 16, wherein the ceramic comprises one of the following: (a) zirconium oxide; or (b) aluminum oxide.

19. The method of claim 1, wherein the implant is a knee implant, a hip implant or a screw implant.

20. The method of claim 1, wherein the implant is a dental implant.

21. A method of applying crystalline nanoparticles onto the surface of an implant to produce an implant having a crystalline nanoparticle layer with a controlled thickness on its surface, the method comprising:
- providing an implant substrate body comprising microtopography on its surface;
- applying crystalline nanoparticles onto the surface of the implant substrate body;
- rotating the implant substrate body;
- directing a pressurized gas stream toward the implant while the implant is rotating to remove excess crystalline nanoparticles;
- forming a crystalline nanoparticle layer with a controlled thickness on the surface of the implant in response to the directing step;
- and substantially retaining the microtopography of the implant surface in response to the applying and rotating steps.

* * * * *

UNITED STATES PATENT AND TRADEMARK OFFICE
CERTIFICATE OF CORRECTION

| | | |
|---|---|---|
| PATENT NO. | : 8,632,843 B2 | Page 1 of 1 |
| APPLICATION NO. | : 12/276664 | |
| DATED | : January 21, 2014 | |
| INVENTOR(S) | : Andersson et al. | |

It is certified that error appears in the above-identified patent and that said Letters Patent is hereby corrected as shown below:

On Title Page:

Item (73), Assignee: Please correct "Promimic AB, Gothenburg (SE)"
to read -- Promimic AB, Goteborg (SE) --

Signed and Sealed this
Fourteenth Day of October, 2014

Michelle K. Lee
*Deputy Director of the United States Patent and Trademark Office*